(12) United States Patent
Cerwin et al.

(10) Patent No.: US 7,467,710 B2
(45) Date of Patent: Dec. 23, 2008

(54) MOLDED PACKAGE

(75) Inventors: Robert Cerwin, Pipersville, PA (US);
Clifford Dey, Riegelsville, PA (US);
Glynn Clements, Greenville, SC (US)

(73) Assignee: Ethicon, Inc., Somerville, NJ (US)

( * ) Notice: Subject to any disclaimer, the term of this patent is extended or adjusted under 35 U.S.C. 154(b) by 559 days.

(21) Appl. No.: 11/121,804

(22) Filed: May 4, 2005

(65) Prior Publication Data

US 2006/0249405 A1  Nov. 9, 2006

(51) Int. Cl.
*A61B 17/06* (2006.01)
(52) U.S. Cl. ................ 206/63.3; 206/499; 220/780
(58) Field of Classification Search ............... 206/63.3, 206/380, 499, 459.1, 459.5, 449, 807; 220/315, 220/345.3, 780, 324; 221/305, 306, 303, 221/309; 229/240

See application file for complete search history.

(56) References Cited

U.S. PATENT DOCUMENTS

| 4,570,818 A | * | 2/1986 | Borst et al. ............. 206/459.5 |
| 4,770,338 A | * | 9/1988 | Tatusch ..................... 206/807 |
| 5,860,517 A | | 1/1999 | Gemma, Jr. et al. |
| 5,971,263 A | * | 10/1999 | Mangano .................. 229/110 |
| 5,988,367 A | | 11/1999 | Gemma, Jr. et al. |
| 6,237,757 B1 | | 5/2001 | Alpern et al. |
| 6,352,170 B1 | * | 3/2002 | Brown et al. ............... 220/315 |
| 6,598,737 B2 | | 7/2003 | Rudnick |
| 2002/0195413 A1 | * | 12/2002 | Eastman et al. ........ 206/459.1 |
| 2004/0245134 A1 | | 12/2004 | Alcouloumre et al. |

FOREIGN PATENT DOCUMENTS

| EP | 0819408 B1 | 10/2003 |
| FR | 2 832 621 A1 | 5/2003 |

* cited by examiner

*Primary Examiner*—Luan K Bui

(57) ABSTRACT

A package assembly and method for packaging sutures is provided. The package includes a substantially rectangular casing defining an internal area therein and including a container portion having a substantially flat bottom side defined by first, second, third and fourth edges, and first, second, third and fourth sides extending upwardly from the first, second, third and fourth edges respectively, and a lid portion removably secured to a top side of the container portion to thereby form an integral casing. The package further includes a plurality of suture packages each having a substantially planar shape, wherein the plurality of packages are positioned within the internal area of the rectangular casing substantially parallel to one another and substantially perpendicular to the bottom side of the container portion. The third side of the container portion, in a region substantially adjacent to the first side of the container portion, includes a removable breakaway portion wherein removal thereof leaves an opening through which the suture packages can be removed.

12 Claims, 10 Drawing Sheets

MOLDED PACKAGE

FIELD OF THE INVENTION

The present invention relates generally to the field of packaging, and more specifically to a new and improved universal package having particular application for surgical sutures, and a method for providing packaging for such sutures.

BACKGROUND OF THE INVENTION

Figure 1A:
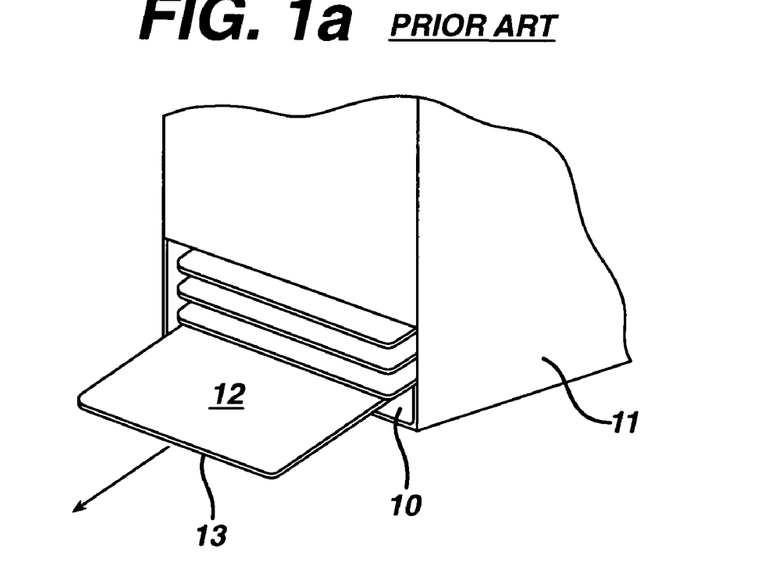
FIG. 1a is a perspective view of a prior art suture dispensing box illustrating dispensing according to the preferred method in the United States.

Surgical sutures are commonly used in a wide variety of surgical procedures. Typically, the sutures are packaged within individual containers such as foil laminate packages. These packages are substantially flat or planar, and multiple individual packages are stacked on one another and provided together in a larger package of "box" to the customer. At the surgical site where the sutures are used, the larger package is typically designed to also serve as a dispenser that provides a means for easily dispensing the smaller packages when needed. The United States and Europe have developed different preferences for how the individual suture packages are dispensed. In the United States, it is preferred to have the smaller suture packages stacked on one another horizontally as shown in FIG. 1a. An opening 10 is provided in the dispensing box 11 so that the suture packages 12 can be removed from the dispensing box by grasping the shorter edge 13 of the bottom most suture package, and withdrawing it out through the opening in the direction shown by the arrow. As this is the preference in the U.S., racks that hold multiple dispensing boxes have been designed specifically to hold the dispensing boxes in the vertical configuration shown.

Figure 1B:
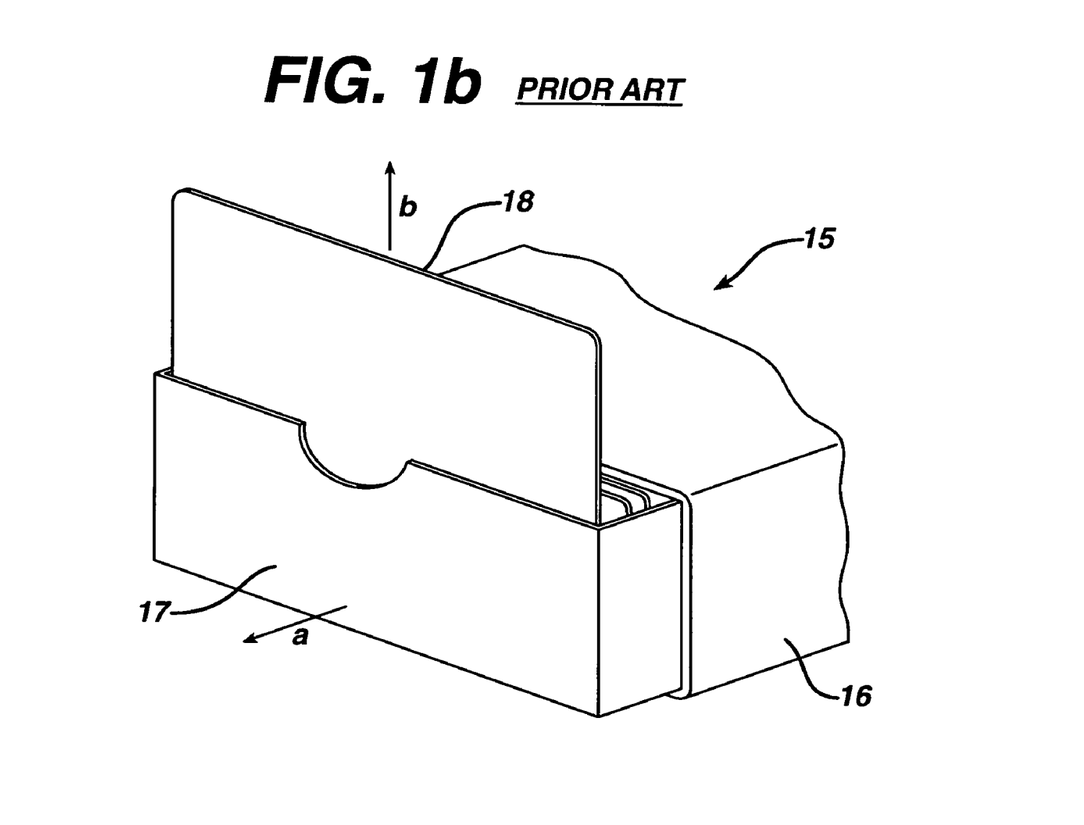
FIG. 1b is a perspective view of a prior art suture dispensing box illustrating dispensing according to the preferred method in Europe.

To the contrary, in Europe the preference is that the dispensing box 15 be positioned horizontally as shown in FIG. 1b so that the dispensing box can be used like a drawer. Often, the dispensing box consists of an outer casing 16 and a drawer 17 that can be slid out from the casing in the direction indicated by arrow a in FIG. 1b. The suture packages are stacked vertically on a long edge 18, and are removed in the direction indicated by arrow b. Based on this preference, European racks have also been designed specifically to hold dispensing boxes in this manner.

In an effort to provide a suture dispensing box that satisfies both the U.S. and European preferences, U.S. Pat. No. 5,860,517 describes a two-piece dispensing box that includes a drawer that slides within a sleeve or outer casing, where the box further includes an opening that enables dispensing according to the U.S. preference. This design, however, it not entirely universal, as additional spacers are required within the package to ensure a proper fit in both the U.S. and European racks. Since U.S. racks are deeper, the package described in the '517 patent, if sized for a European rack, would sit back too far in a U.S. rack. To address this, the package includes a drawer dimensioned for a European rack in combination with a sleeve dimensioned for a U.S. rack. The open space within the oversized sleeve is filled with a spacer. Thus, the device disclosed by the '517 patent requires a two-piece configuration in combination with the extra spacer that serves no other useful purpose.

Most known surgical dispensing boxes are also made of paperboard. Paperboard must be stamped out in two dimensions, then subsequently folded and erected, requiring separate machinery and automation for the latter. This process typically results in waste of approximately 7-10% due to boxes that are crushed or damaged. Further, since folding does not yield a tight fit of corners and/or sides, paperboard boxes often must be delivered in a cellophane wrapper in order to minimize dust or other particulates from entering the package. Finally, as will be described further below, product tampering and counterfeiting issues are difficult problems facing the industry today. Paperboard boxes have proven less than optimal in dealing with these problems. Although suture dispensing boxes have been known to be formed from molded plastic, none are known to satisfy the need for a universal dispensing box, and all have required multiple moving parts to accomplish dispensing needs.

SUMMARY OF THE INVENTION

The present invention provides a package assembly including a substantially rectangular casing defining an internal area therein and including a container portion having a substantially flat bottom side defined by first, second, third and fourth edges, and first, second, third and fourth sides extending upwardly from the first, second, third and fourth edges respectively. The package further includes a lid portion removably secured to a top side of the container portion to thereby form an integral casing, and a plurality of suture packages each having a substantially planar shape. The suture packages are positioned within the internal area of the rectangular casing substantially parallel to one another and substantially perpendicular to the bottom side of the container portion. The third side of the container portion, in a region substantially adjacent to the first side of the container portion, includes a removable breakaway portion wherein removal thereof leaves an opening through which the suture packages can be removed.

The present invention also provides a package assembly holding a plurality of suture packages therein having a container portion including a substantially planar bottom side having a periphery defined by first, second, third and fourth edges, and first, second, third and fourth sides extending upwardly from the first, second, third and fourth edges respectively. The first and second sides are substantially parallel to one another and substantially perpendicular to the bottom side, and the third and fourth sides are substantially parallel to one another and substantially perpendicular to the bottom side and the first and second sides. The third side, in a region substantially adjacent to the first side and extending substantially a width of the third side, further includes a removable breakaway portion wherein removal thereof leaves an opening through which the suture packages may pass. The package assembly further includes a lid portion removably secured to the container portion by at least one engagement device. The lid portion is positioned substantially parallel to the bottom side and has a substantially similar periphery to that of the bottom side. The lid portion in combination with the container portion forms a substantially rectangular shape having an internal area for holding the plurality of suture packages. Also included is a label affixed to an exterior of the package assembly and positioned either substantially across the breakaway portion so as to prevent removal thereof but so as not to prevent removal of the lid portion, or across a sufficient portion of the lid portion and at least one of the first, second, third and fourth sides of the container portion so as to prevent removal of the lid portion from the container portion but so as not to prevent removal of the breakaway portion.

Yet another package for holding a plurality of suture packages is provided herein having a molded plastic container portion including a substantially planar bottom side, first, second, third and fourth sidewalls extending upwardly from first, second, third, and fourth edges of the bottom side respectively, and an open top side collectively defining an internal area therein, and having at least one engagement element. It further includes a molded plastic lid portion having a substantially planar configuration and having at least one engagement element. The at least one engagement element of the container portion and the at least one engagement element of the lid portion are removably engaged with one another to thereby removably secure the lid portion to the container portion to thereby form an integral package that substantially encloses the internal area, and that when removed, allows access to the suture packages therein. The third sidewall further includes a removable breakaway portion wherein removal thereof leaves an opening through which at least one of the plurality of suture packages may pass.

Finally, a method is provided for providing a package assembly including a plurality of suture packages enclosed therein. The method involves molding plastic to form a container portion having a substantially planar bottom side including a periphery defined by first, second, third and fourth edges, and having first, second, third and fourth sides extending upwardly from the first, second, third and fourth edges respectively. The first and second sides are substantially perpendicular to the bottom side and substantially parallel to one another, and the third and fourth sides are substantially parallel to one another, and substantially perpendicular to the bottom side and to the first and second sides. The container portion has a removable breakaway portion in the third side in an area substantially adjacent to the first side. The method further involves molding plastic to form a lid portion having a substantially planar configuration including a periphery that is substantially similar to the periphery of the bottom side of the container portion, providing a plurality of suture packages having a substantially planar configuration, inserting the plurality of suture packages within an internal area of the container portion such that the suture packages are aligned substantially parallel to one another and to the first and third sides of the container portion, removably securing the lid portion to the container portion to thereby form an integral package, and affixing a label either in a first position on an exterior of the package assembly that prevents access to the breakaway portion, but does not prevent removal of the lid portion from the container portion, or in a second position on the exterior of the package assembly that prevents removal of the lid portion from the container portion, but does not prevent access to the breakaway portion.

These and other objects, features and advantages of the present invention will be apparent from the following detailed description of illustrative embodiments thereof, which is to be read in connection with the accompanying drawings.

DETAILED DESCRIPTION

Although the invention is described herein in conjunction with packaging of surgical sutures, the invention is not so limited. The features and advantages achieved by the present invention have applicability for packaging various other types of surgical elements or devices, as well as to packaging of various other types of items.

Figure 2:
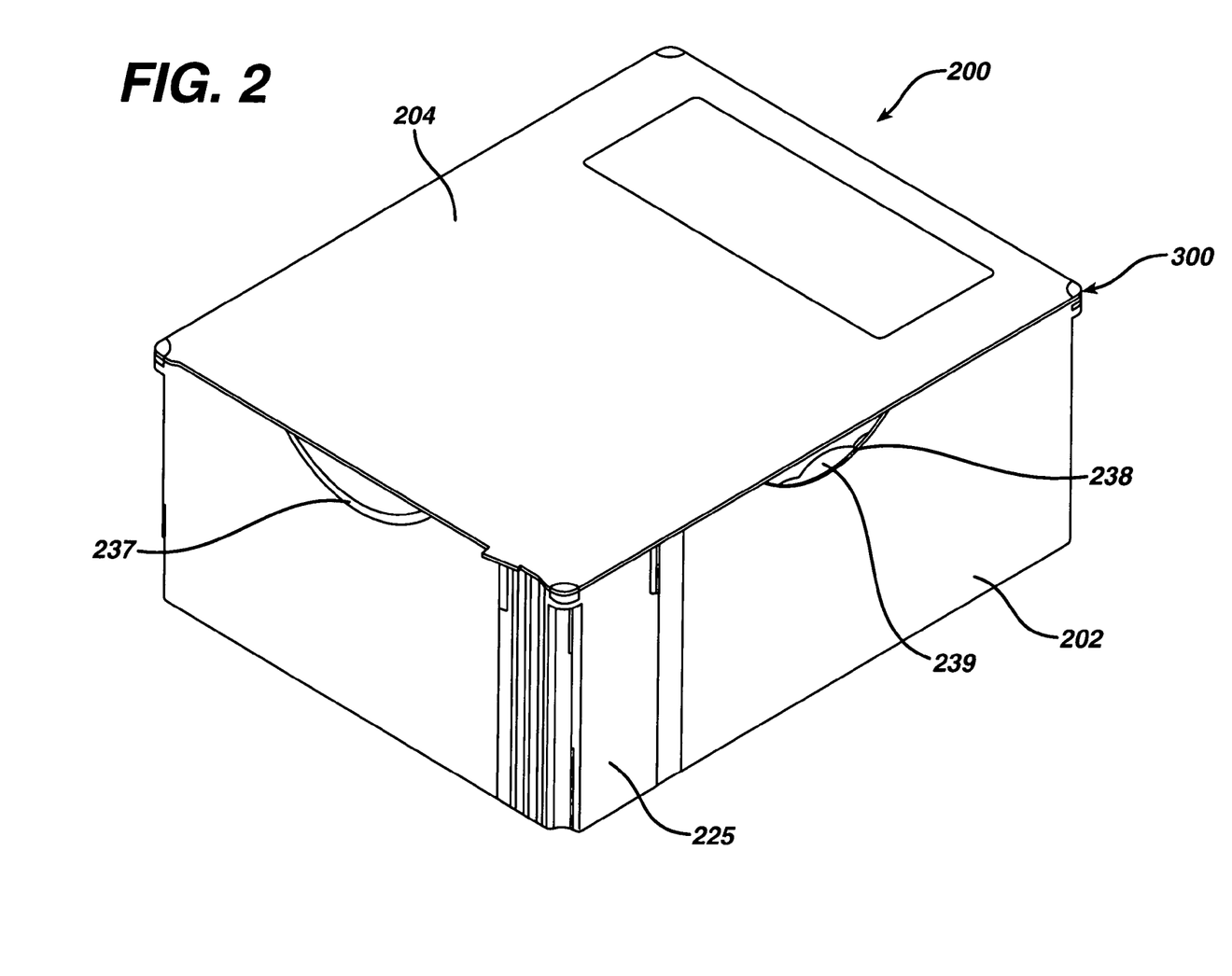
FIG. 2 is a perspective view of one embodiment of a package according to the present invention.
Figure 3:
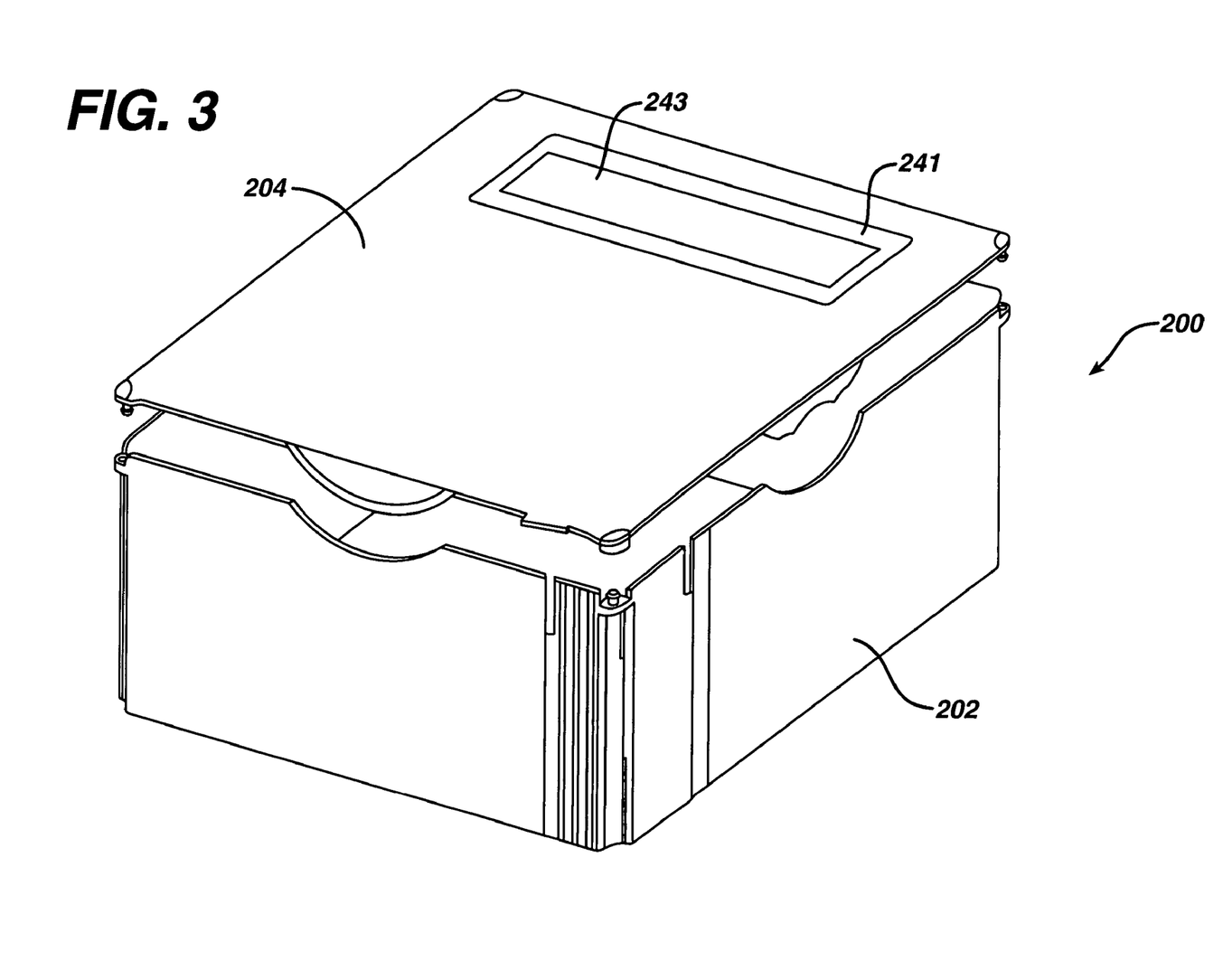
FIG. 3 is an exploded view of FIG. 2 illustrating the lid portion separated from the container portion.
Figure 4:
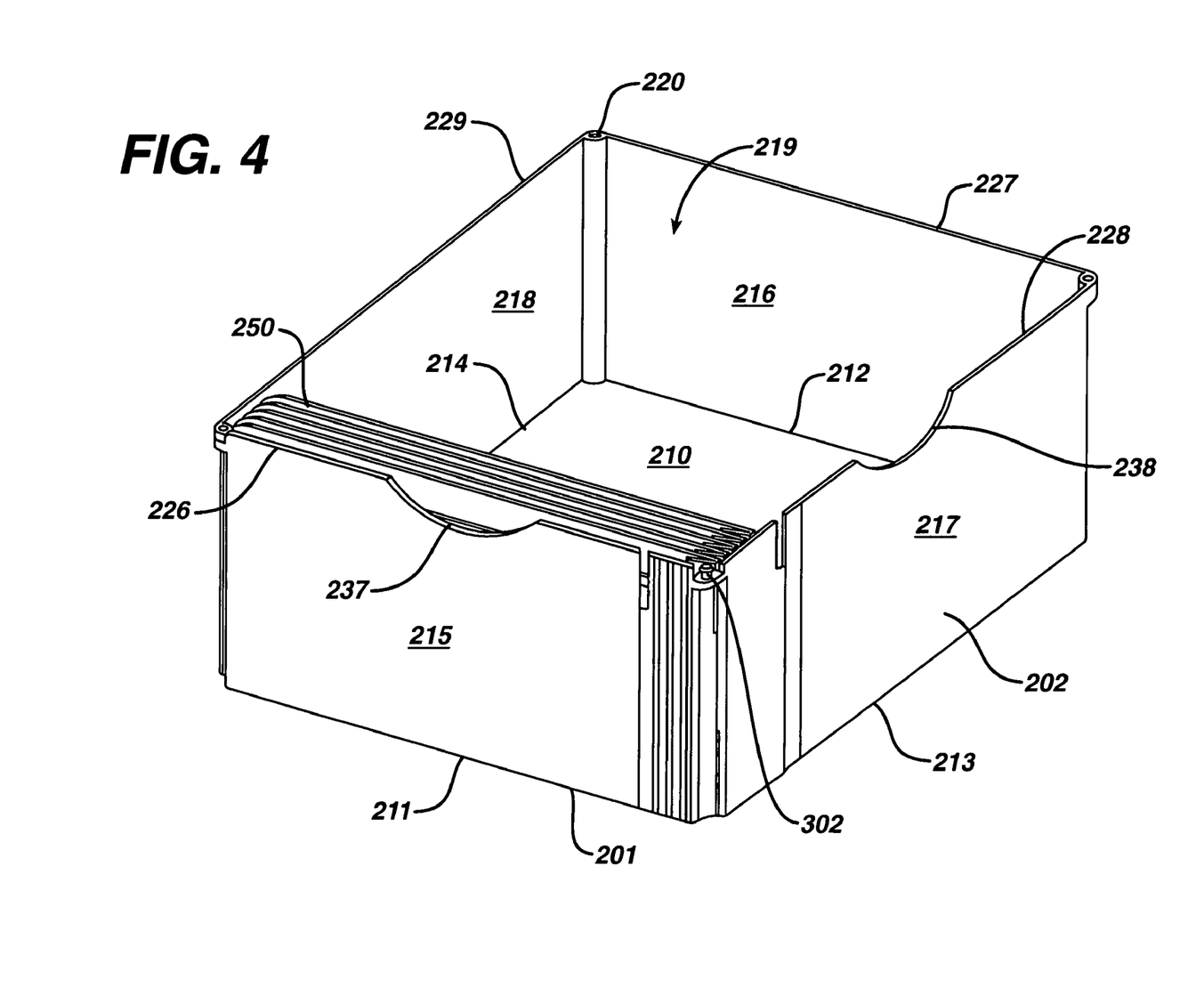
FIG. 4 is a perspective view of the container portion of the package of FIG. 2.

Referring now to FIG. 2, one embodiment of the present invention provides a package or casing 200 made of molded plastic (as described further below) including a container portion 202 and a lid portion 204. When fully constructed, the lid portion 204 is removably coupled to the container portion (see FIG. 3) as will be described further below. As shown in FIG. 4, the illustrated container portion 202 includes a substantially planar bottom side 210 having an outer periphery 201 defined by first and second opposite edges 211, 212, and third and fourth opposite edges 213, 214 that are substantially perpendicular to, but preferably longer than, the first and second opposite edges. The container portion further includes first and second sides or sidewalls 215, 216 extending upwardly from the bottom side 210 at its first and second bottom edges 211, 212 such that they are substantially parallel to one another and substantially perpendicular to the bottom side as shown. Similarly, third and fourth sides 217, 218 extend upwardly from the bottom side at its third and fourth edges 213, 214 and are substantially parallel to one another, but substantially perpendicular to the first and second sides and the bottom side. Thus, the bottom side, in conjunction with the first, second, third and fourth sides, define an inner area 219 within which individual suture packages 250 or other elements are contained.

Figure 5:
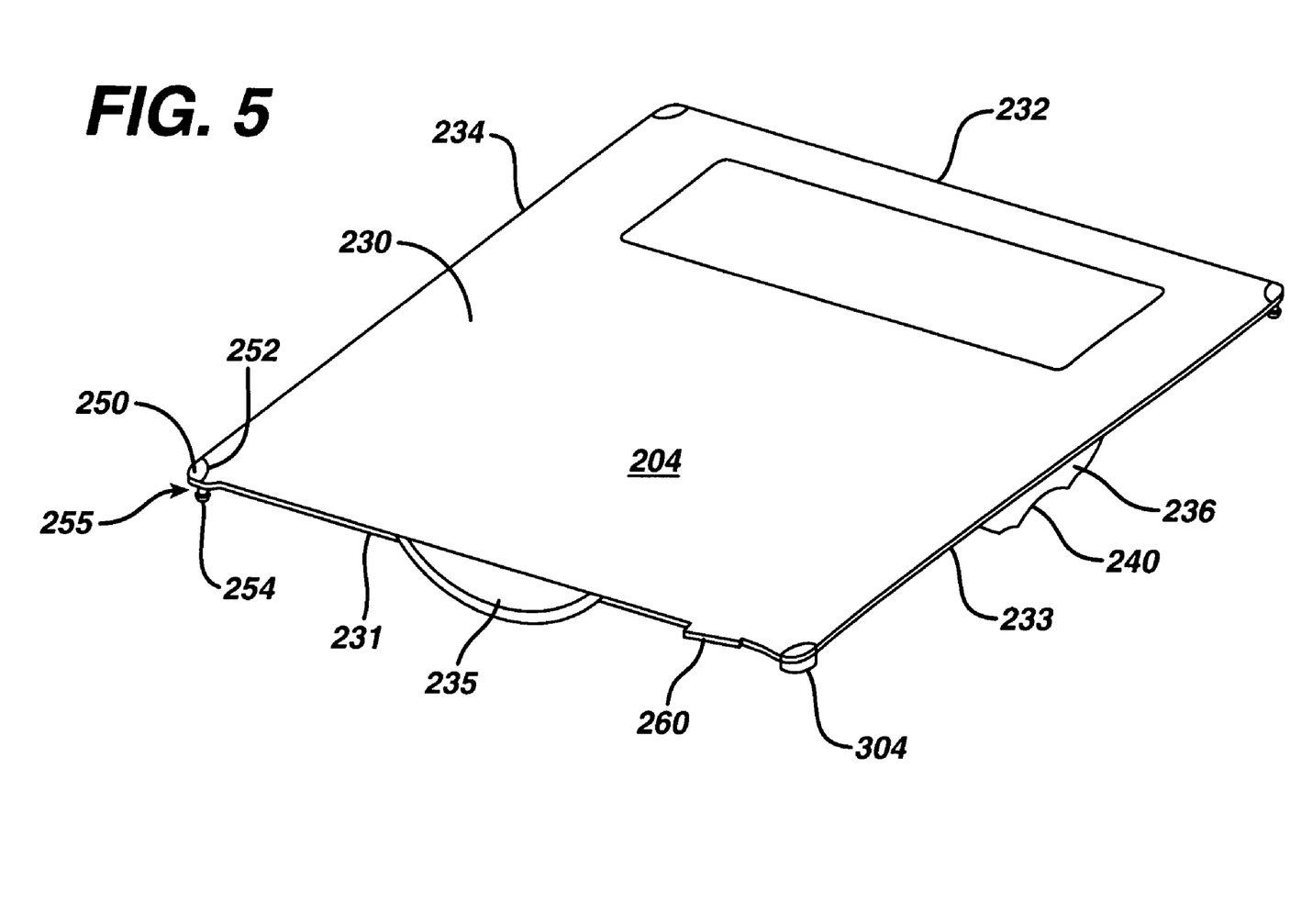
FIG. 5 is a top perspective view of the lid portion of the package of FIG. 2.

The lid portion is illustrated separately in FIG. 5, and consist primarily of a substantially flat or planar top side 230 having a periphery substantially the same as the bottom side of the container portion so that its first 231, second 232, third 233 and fourth 234 edges substantially align with the top edges 226, 227, 228, 229 of the first, second, third, and fourth sides of the container portion respectively. Preferably, the top side further includes first and second tab portions 235, 236 extending downwardly therefrom such that, when the lid portion is coupled with the container portion as shown in FIG. 2, they substantially align with and are complementary to recesses 237, 238 in the first and third sides of the container portion. Tab portion 236 may further include a recess 240 to facilitate finger access for subsequent removal of the lid portion.

After the contents of the package (i.e., sutures packages 250) are loaded within the container portion, the lid portion is removably secured to the container portion so as to substantially enclose the internal area 219. One mechanism by which this can be achieved is by one or more engagement devices 300. In a preferred embodiment, the engagement devices include one or more protrusions 302 (see FIG. 4) extending upwardly from the top periphery of the container portion, and a corresponding number of recesses (not shown directly, but the position of one is shown generally by reference numeral 304 in FIG. 5) in the lid portion. The protrusions are positioned along the top periphery of the container portion so as to engage the recesses in the lid portion. The protrusions and recesses are dimensioned relative to one another to from a tight snap fit that secures the lid portion to the container portion, but, with sufficient force from a user, enables the snap fit to be broken to thereby later separate the lid portion from the container portion if desired. Removal of the lid portion from the container portion can be facilitated by a small opening 239 or the like adjacent to the lid portion (for example, formed by the recess 240 in tab portion 236 as described above) through which a user can at least partially insert a finger or other element to apply pressure against the lid portion to separate it from the container portion. Referring back to FIGS. 2-6, in the illustrated embodiment, three engagement devices are shown, each located substantially at the intersection of successive sides of the container portion (i.e., between the second and fourth sides).

Figure 9:
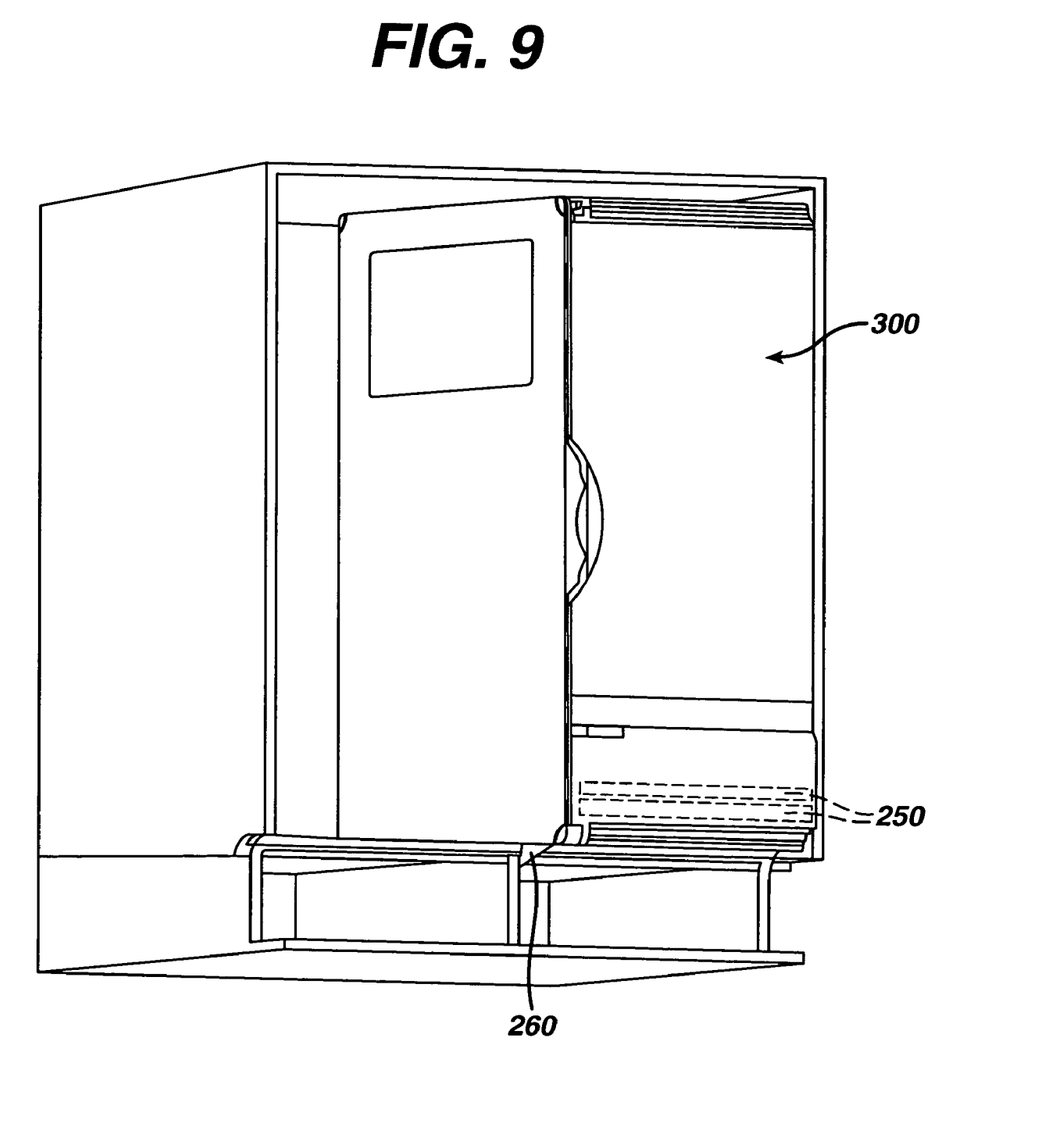
FIG. 9 is a perspective view illustrating the package of FIG. 2 within a typical U.S. rack.

In a preferred embodiment, the third side 217 of the container portion, preferably in a location substantially adjacent to the first side, further includes a breakaway portion 225 that is designed, upon application of a predetermined force by a user, to break away, or at least partially break away from, the remainder of the container portion so as to leave an opening 335 through which the contents of the package can be removed as shown in FIG. 9. For suture packages, the remaining opening 335 is preferably dimensioned to allow removal of the suture package via its short edge as shown, so that the package can be used to dispense sutures in the preferred U.S. manner.

Figure 6:
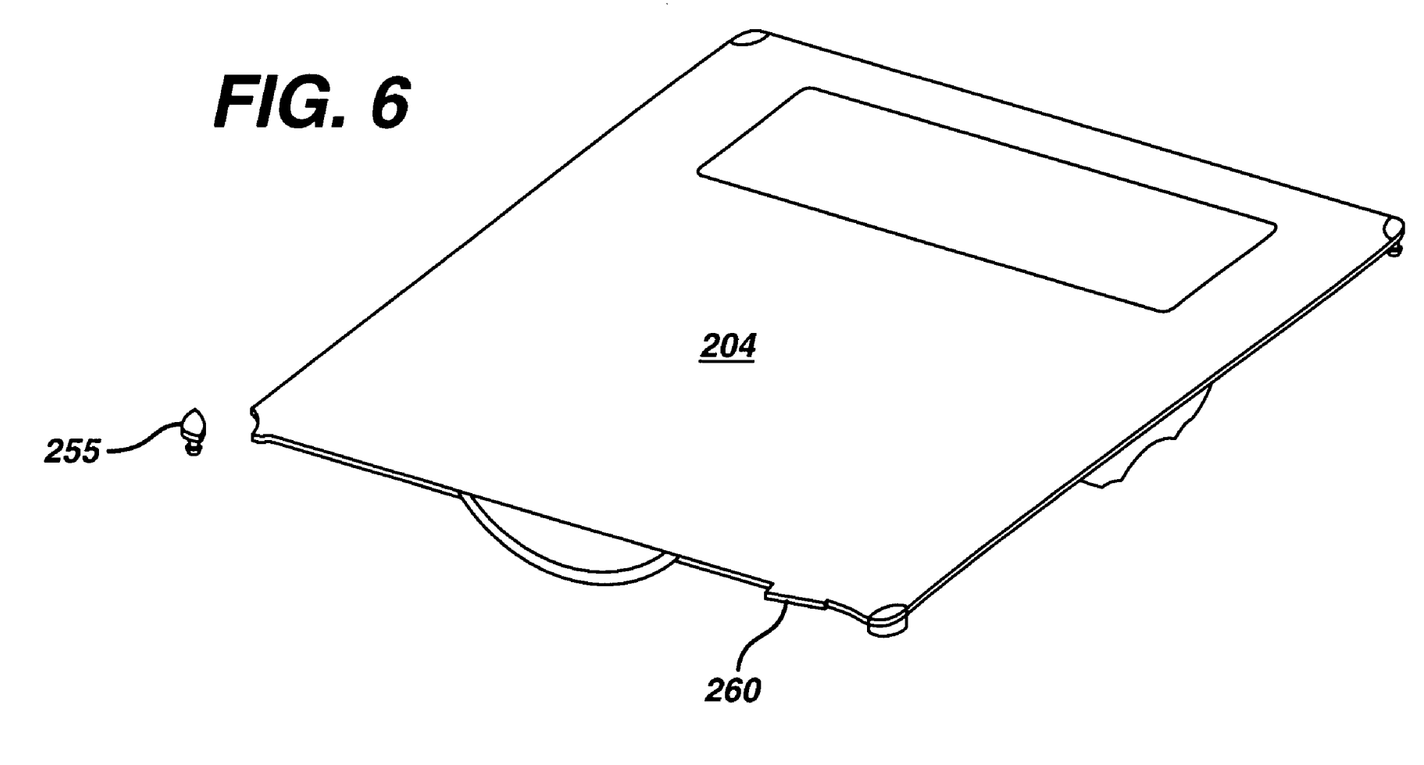
FIG. 6 illustrates a tamper resistant feature within the package of FIG. 2.

An additional feature that may be incorporated into the package is illustrated further with reference to FIGS. 5 and 6. As shown, one corner of lid portion 204 includes tamper indicator portion 255 that is designed to fracture or break away from the lid portion when the lid portion is removed from the container portion. This may be accomplished by any suitable means, such as by providing a weakened attachment line 252 between the tamper indicator portion 255 and the lid portion 204 which will fracture before the engagement element 254 allows release of the lid portion from the container portion. In this manner, the lid portion cannot subsequently be re-secured to the container portion, which can indicate that the package has been tampered with.

As stated previously, most known packages for surgical sutures are comprised of paperboard. The molded plastic design according to the present invention enables multiple advantageous features to be designed into the package that would not be possible with paperboard packages. First, the plastic package is molded directly into its three dimensional configuration, thereby eliminating the additional cumbersome steps of subsequently folding and erecting a two dimensional cut out as is done with paperboard packaging. The nature of plastic molding also allows for varying wall thickness if necessary or desired. The resulting plastic product is also rigid as opposed to flexible paperboard, which provides a product that is less likely to be damaged during shipping. Further, the present invention can utilize the rigidity of the plastic to provide a truly universal box that can readily fit into U.S. or European racks. A protrusion 260 or the like can be designed into the lid portion that will engage the bottom edge of a U.S. rack as shown in FIG. 9 to prevent the box from being pushed too far back into the rack. As indicated above, with the universal box disclosed in U.S. Pat. No. 5,860,517, a separate spacer is required to prevent this from happening. As an alternative, with plastic the shape of the box could be configured such that the box achieves a press fit within the rack (typical racks are tapered inward from front to back) before moving too far rearward, which is possible only because of the rigidity of plastic versus paperboard.

According to preferred embodiments of the present invention, the box disclosed herein also can readily provide counterfeiting protection in ways not possible with traditional paperboard boxes. With plastic, during the molding process various anti-counterfeiting features can be incorporated directly into the box. At its most basic form, color coding or the like can be incorporated into the plastic at various predetermined locations. These features are very difficult to accurately duplicate, thus better preventing counterfeiting. Molded plastic also readily allows etching of the box using a laser, hot stamp or the like, which can be used to designate country of sale or other destination in an effort to prevent diversion. More complicated anti-counterfeiting devices can also easily be incorporated, such as molding RFIDs (radio frequency identification disks), sound indicators etc. directly into the box.

Finally, the versatility of plastic provides a variety of advantages associated with labeling. For example, the ability to vary wall thickness enables labels to be recessed relative to the outer surface of the package. With current paperboard packages, labels are placed on top of the package surface. This type of arrangement leaves the labels prone to scuffing or the like during shipping and handling. Referring to FIG. 3, recessed region 241 may take on any configuration suitable to receive therein a standard label 243. The depth of the recess should be sufficient so that the surface of the label is even with or below the surface of the remainder of the lid portion so that it is protected from chafing against other packages.

Figure 7:
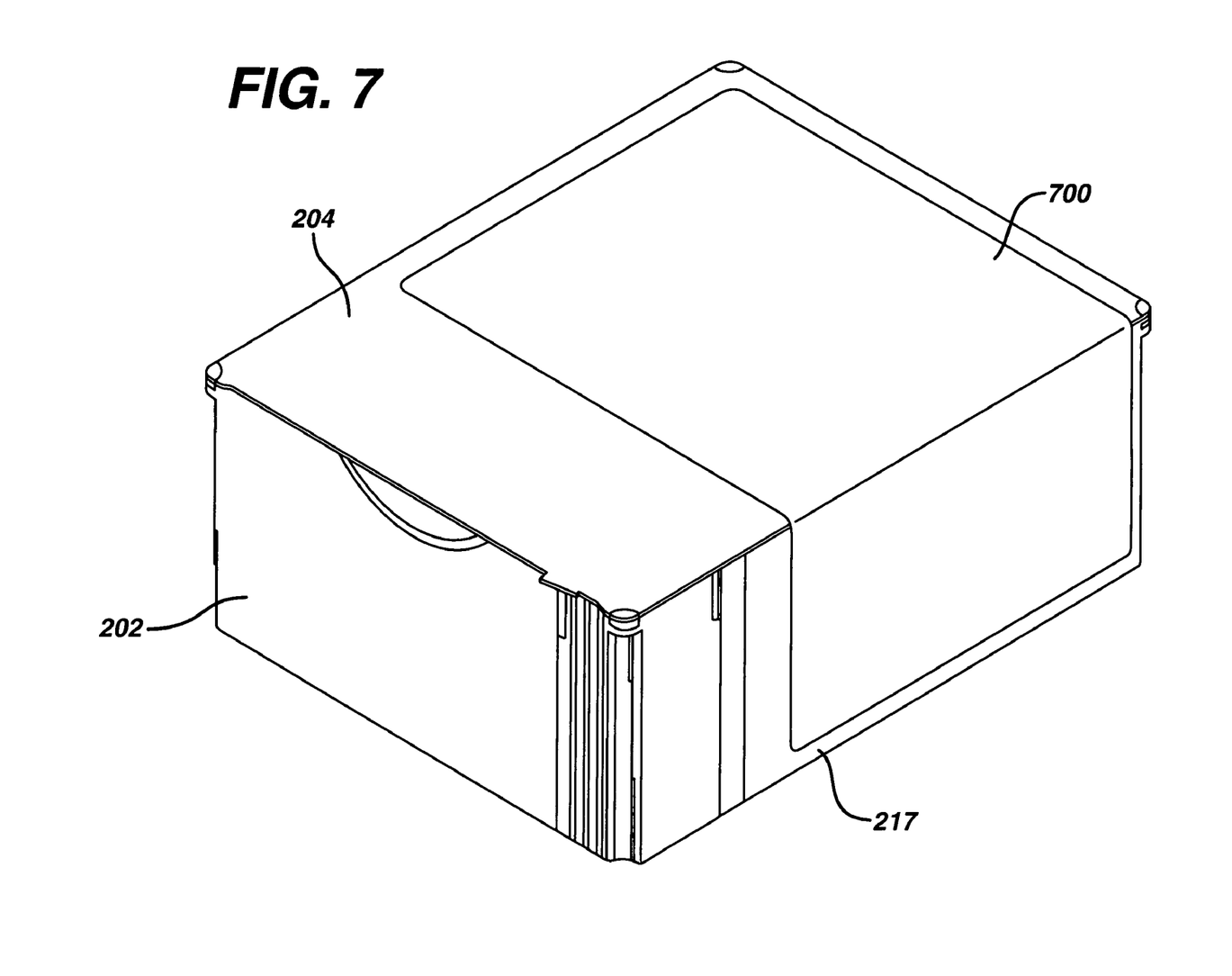
FIG. 7 is a perspective view of the package of FIG. 2 including a label in a first position.
Figure 8:
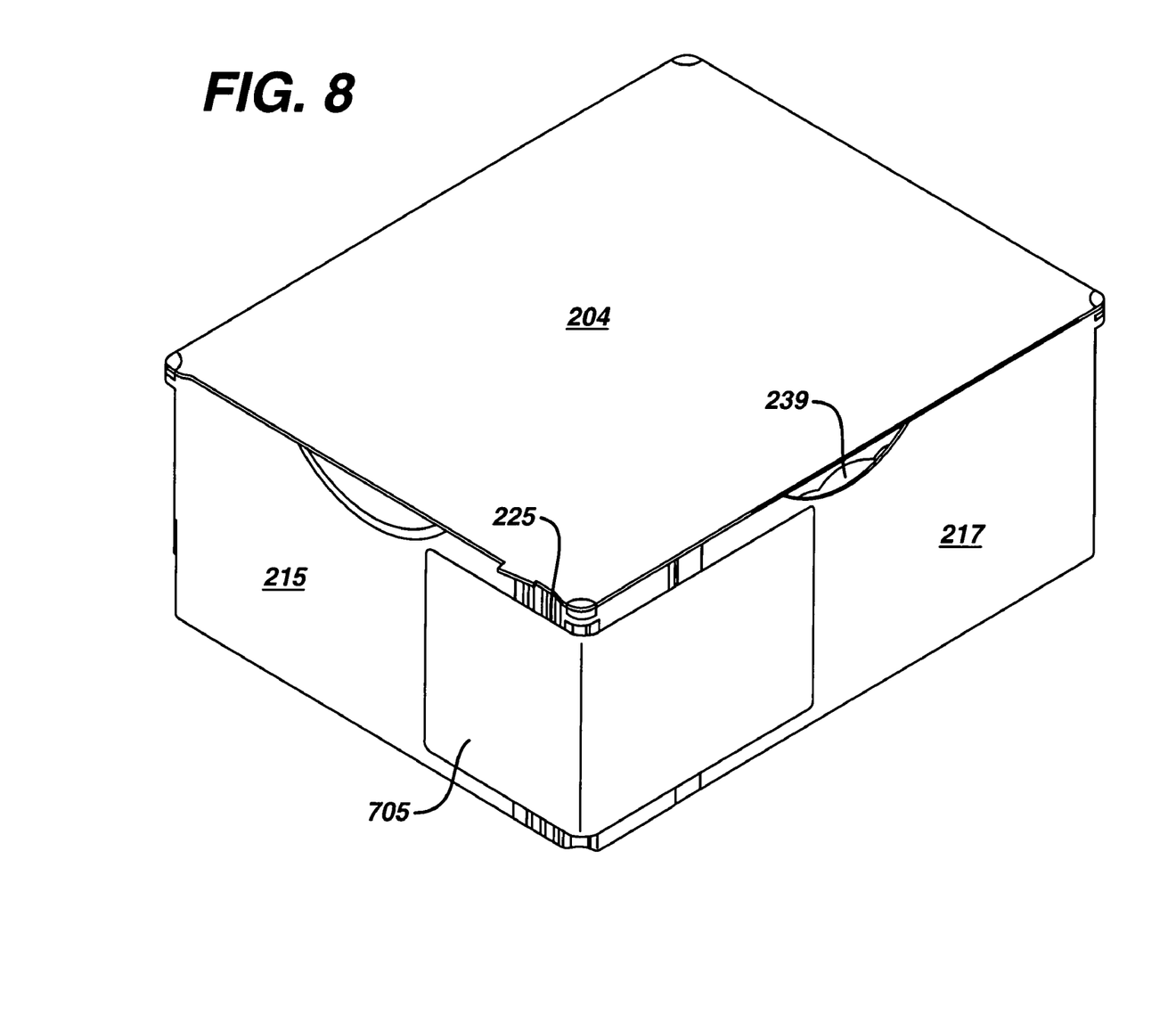
FIG. 8 is a perspective view of the package of FIG. 2 including a label in a second position.
Figure 10:
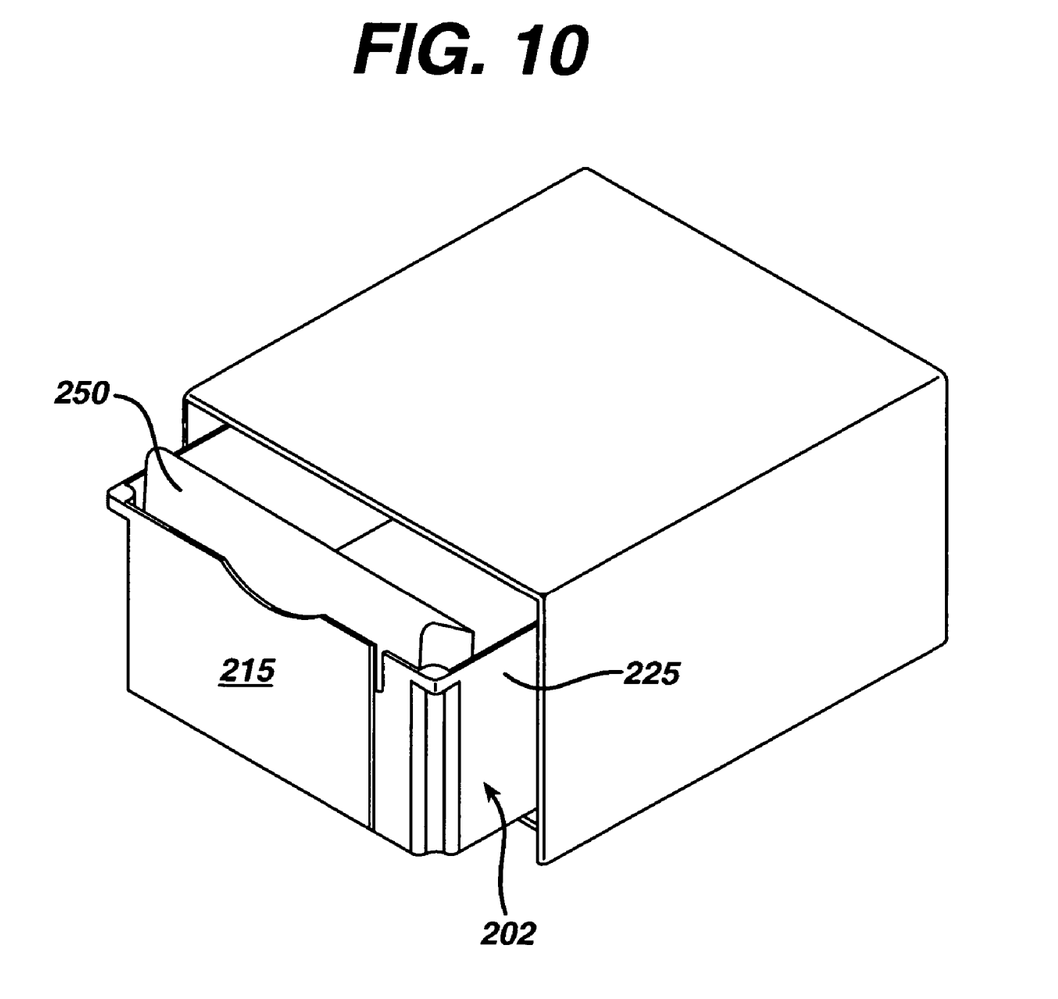
FIG. 10 is a perspective view illustrating the package of FIG. 2 within a typical European rack.

The package assembly described herein also provides extensive cost savings for manufacturing and distribution. It is envisioned that the package assembly will be manufactured and assembled as shown in FIG. 2, with individual suture packages loaded therein in the manner indicated in FIG. 4 prior to securing the lid portion to the container portion. The assembly will then remain within a warehouse or distribution center until its end customer, or at least end customer location (i.e, country or region) is identified. At that time, an appropriate label for that customer or end location can be affixed to the package assembly in a manner specific to that customer. For example, if the designated customer or desired end location is in the United States, a label such as that shown in FIG. 7 is secured to the assembly in the manner shown. The label 700 should be affixed to the outside of the package assembly so as to prevent a customer from removing the lid portion 204 from the container portion 202, but so as not to obstruct access to breakaway portion 225. Preferably, the label is placed across a portion of the lid portion as shown, and extends down over one or more of the adjacent sides, such as third side 217 to thereby help prevent separation of the lid portion from the sides. The label 700 should preferably further prevent access to any feature that facilitates removal of the lid portion, such as opening 239 shown in FIG. 2. In this manner, the end user can only access the suture packages within through breakaway portion 225 to enable dispensing in the preferred U.S. manner as is further illustrated in FIG. 9. If the designated end user or end location is in Europe or utilizes the European style of dispensing sutures, the label will be affixed in a manner such as that shown in FIG. 8 so as to impair access to the breakaway portion, but not to impede a customer from removing the lid portion from the container portion. For example, in the illustrated embodiment the label 705 extends from the first side 215 to the second side 217, and in doing so substantially covers breakaway portion 225, but does not extend over the lid portion 204 or opening 239 that facilitates removal of the lid portion by a customer. Thus, the label prevents the end user from accessing the suture packages within through the breakaway portion 225, but instead enables access by removing the lid portion 204 from the container portion 202. FIG. 10 illustrates such a package used for dispensing in the preferred European manner.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. A package assembly comprising:
   a substantially rectangular casing defining an internal area therein and including a container portion having a substantially flat bottom side defined by first, second, third and fourth edges, and first, second, third and fourth sides extending upwardly from the first, second, third and fourth edges respectively, and a lid portion removably secured to a top side of the container portion to thereby form an integral casing;
   a plurality of engagement devices including a plurality of protrusions in one of said container portion or lid portion, and a plurality of recesses in the other of said container portion and lid portion, wherein each of said plurality of protrusions are press fit within a respective one of said plurality of recesses to removably secure the container portion to the lid portion; and
   a plurality of suture packages each having a substantially planar shape, wherein the plurality of packages are positioned within the internal area of the rectangular casing substantially parallel to one another and substantially perpendicular to the bottom side of the container portion;
   wherein the third side of the container portion, in a region substantially adjacent to the first side of the container portion, includes a removable breakaway portion wherein removal thereof leaves an opening through which the suture packages can be removed.

2. The package assembly according to claim 1 wherein the rectangular casing is comprised of molded plastic.

3. The package assembly according to claim 1, wherein each of the first, second, third and fourth sides of the container portion are substantially perpendicular to the bottom side of the container portion, and wherein the first and second sides are substantially parallel to one another and the third and fourth sides are substantially parallel to one another.

4. The package assembly according to claim 3, wherein the lid portion is substantially parallel to the bottom side of the container portion and has a substantially similar shape as the bottom side of the container portion.

5. The package assembly according to claim 1, wherein the lid portion is removably secured to the container portion by at least one engagement device, and wherein the casing further includes a tamper indicator portion that fractures or breaks away from the casing when the lid portion is removed from the container portion.

6. The package assembly according to claim 1, wherein at least one of the sides of the container portion further comprises, in an area adjacent the lid portion, an aperture or recess therein.

7. The package assembly according to claim 1, further comprising a label affixed to the casing in a position that substantially covers the breakaway portion to thereby prevent removal of the breakaway portion, but does not obstruct removal of the lid portion from the container portion.

8. The package assembly according to claim 1, further comprising a label affixed to the casing in a position that prevents removal of the lid portion from the container portion, but does not obstruct access to the breakaway portion.

9. The package assembly according to claim 1, further comprising a projection extending distally beyond the first side of the container portion at a location substantially proximal to the third side of the container portion.

10. The package assembly according to claim 9, wherein the projection extends from the lid portion.

11. A package assembly holding a plurality of suture packages therein comprising:
    a container portion including a substantially planar bottom side having a periphery defined by first, second, third and fourth edges, and first, second, third and fourth sides extending upwardly from the first, second, third and fourth edges respectively, the first and second sides being substantially parallel to one another and substantially perpendicular to the bottom side, and the third and fourth sides being substantially parallel to one another and substantially perpendicular to the bottom side and the first and second sides, wherein the third side, in a region substantially adjacent to the first side and extending substantially a width of the third side, further includes a removable breakaway portion wherein removal thereof leaves an opening through which the suture packages may pass; and
    a lid portion removably secured to the container portion by at least one engagement device, the lid portion being positioned substantially parallel to the bottom side and having a substantially similar periphery to that of the bottom side, wherein the lid portion in combination with the container portion forms a substantially rectangular shape having an internal area for holding the plurality of suture packages;
    a plurality of engagement devices including a plurality of protrusions in one of said container portion or lid portion, and a plurality of recesses in the other of said container portion and lid portion, wherein each of said plurality of protrusions are press fit within a respective one of said plurality of recesses to removably secure the container portion to the lid portion; and
    a label affixed to an exterior of the package assembly and positioned either substantially across the breakaway portion so as to prevent removal thereof but so as not to prevent removal of the lid portion, or across a sufficient portion of the lid portion and at least one of the first, second, third and fourth sides of the container portion so as to prevent removal of the lid portion from the container portion but so as not to prevent removal of the breakaway portion.

12. The package assembly according to claim 11, wherein the container portion and lid portion are comprised of molded plastic, and wherein the lid portion in combination with the container portion, when removably secured thereto, forms an integral structure.

* * * * *